(12) United States Patent
Hirano et al.

(10) Patent No.: US 12,251,392 B2
(45) Date of Patent: *Mar. 18, 2025

(54) DEOXYNUCLEOSIDE THERAPY FOR DISEASES CAUSED BY UNBALANCED NUCLEOTIDE POOLS INCLUDING MITOCHONDRIAL DNA DEPLETION SYNDROMES

(71) Applicant: The Trustees of Columbia University in the City of New York, New York, NY (US)

(72) Inventors: Michio Hirano, New York, NY (US); Caterina Garone, Cambridge (GB); Ramon Marti, Barcelona (ES)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 18/138,432

(22) Filed: Apr. 24, 2023

(65) Prior Publication Data
US 2023/0277577 A1 Sep. 7, 2023

Related U.S. Application Data

(60) Division of application No. 17/242,822, filed on Apr. 28, 2021, now Pat. No. 11,666,592, which is a continuation of application No. 16/583,852, filed on Sep. 26, 2019, now Pat. No. 11,110,111, which is a continuation of application No. 15/736,092, filed as application No. PCT/US2016/038110 on Jun. 17, 2016, now Pat. No. 10,471,087.

(60) Provisional application No. 62/180,914, filed on Jun. 17, 2015.

(51) Int. Cl.
| | | |
|---|---|---|
| *A61K 31/7072* | (2006.01) |
| *A61K 9/00* | (2006.01) |
| *A61K 31/513* | (2006.01) |
| *A61K 31/7068* | (2006.01) |
| *A61K 31/7076* | (2006.01) |
| *A61K 31/708* | (2006.01) |
| *A61K 45/06* | (2006.01) |
| *A61P 21/00* | (2006.01) |
| *A61P 43/00* | (2006.01) |

(52) U.S. Cl.
CPC ........ *A61K 31/7072* (2013.01); *A61K 9/0053* (2013.01); *A61K 31/513* (2013.01); *A61K 31/7068* (2013.01); *A61K 31/7076* (2013.01); *A61K 31/708* (2013.01); *A61K 45/06* (2013.01); *A61P 21/00* (2018.01); *A61P 43/00* (2018.01)

(58) Field of Classification Search
CPC ........ A61P 21/00; A61P 43/00; A61K 31/513; A61K 31/7068; A61K 31/7072; A61K 31/7076; A61K 31/708
See application file for complete search history.

(56) References Cited

U.S. PATENT DOCUMENTS

| | | | |
|---|---|---|---|
| 6,596,700 B2 | 7/2003 | Sommadossi | |
| 10,292,996 B2 | 5/2019 | Hirano et al. | |
| 10,471,087 B2 * | 11/2019 | Hirano | ............ A61P 43/00 |
| 11,110,111 B2 * | 9/2021 | Hirano | ............ A61K 9/0053 |
| 11,666,592 B2 * | 6/2023 | Hirano | ............ A61K 31/7068 |
| | | | 514/50 |

FOREIGN PATENT DOCUMENTS

| | | |
|---|---|---|
| EA | 005890 | 6/2005 |
| EP | 3 302 499 | 4/2018 |
| RU | 2300381 | 6/2007 |
| WO | WO 2012/0125848 | 9/2012 |

OTHER PUBLICATIONS

Glick, et al., "Molecular Biotechnology: Principles and Applications", Moscow, "Mir", 2002, p. 103, Reference is believe to predate application priority date.

Saada et al., "Mitochondrial deoxyribonucleotide pools in deoxyguanosine kinase deficiency", Molecular Genetics and Metabolism. Academic Press. Amsterdam. NL. vol. 95. No. 3. Nov. 1, 2008 (Nov. 1, 2008). pp. 169-173. XP025546368. ISSN: 1096-7192. DOI: 10.1016/J.YMGME.2008.07.007 [retrieved on Aug. 23, 2008] * p. 171. left-hand column. Paragraph third—p. 172. right-hand column *.

Cowan M J et al: "Deoxycytidine therapy in two patients with adenosine deaminase deficiency and severe immunodeficiency disease", Clinical Immunology and Immunopathology, San Diego, CA, US, vol. 37, No. 1, Oct. 1, 1985 (Oct. 1, 1985), pp. 30-36, XP026224621.

Y. Camara et al: "Administration of deoxyribonucleosides or inhibition of their catabolism as a pharmacological approach for mitochondrial DNA depletion syndrome", EPO Form 1703 01.91TRI Human Molecular Genetics, vol. 23, No. 9, May 1, 2014 (May 1, 2014), pp. 2459-2467, XP055228156.

(Continued)

*Primary Examiner* — Pancham Bakshi
(74) *Attorney, Agent, or Firm* — Amster, Rothstein & Ebenstein LLP

(57) ABSTRACT

The invention relates generally to a pharmacological therapy for human genetic diseases, specifically those characterized by unbalance nucleotide pools, more specifically mitochondrial DNA depletion syndromes, and more specifically, thymidine kinase 2 (TK2) deficiency. The pharmacological therapy involves the administration of at least one deoxynucleoside, or mixtures thereof. For the treatment of TK2 deficiency, the pharmacological therapy involves the administration of either deoxythymidine (dT) or deoxycytidine (dC), or mixtures thereof. This administration of deoxynucleosides is applicable to other disorders of unbalanced nucleotide pools, especially those found in mitochondrial DNA depletion syndrome.

9 Claims, 7 Drawing Sheets

(56) References Cited

OTHER PUBLICATIONS

Julia Wang et al: "TK2-Related Mitochondrial DNA Maintenance Defect, Myopathic Form—GeneReviews—NCBI Bookshelf" In: "Gene Reviews", Dec. 6, 2012 (Dec. 6, 2012), XP055520605.
Steve Perrin: "Make mouse studies work" Nature, vo. 507, p. 423-425, Mar. 27, 2014.
NIH Research Portfolio ONline Reporting Tools (RePORT), project #3—Pharmacological and gene therapy of TK2 deficiency in mice and human, Michio Hirano (accessed Jan. 30, 2018).
Garone et al., "Deoxypyrimidine monophosphates treatment for thymidine kinase 2 deficiency", Neurology, suppl. MeetingAbstracts 80.1, 65th American Acadamy of Neurology Annual Meeting, (Feb. 12, 2013), accessed Jan. 30, 2018.
Akman, Hasan O. "Thymidine kinase 2 (H126N) knockin mice show the essential role of balanced deoxynucleotide pools for mitochondrial DNA maintenance", Human Molecular Genetics, May 8, 2008, vol. 17, No. 16, pp. 2433-2440.
Longley, et al. (May 4, 2006). Mutant POLG2 disrupts DNA polymerase gamma subunits and causes progressive external ophthalmoplegia. Am J Hum Genet. 78:1026-1034.
Martí, et al. (2012b) Assessment of thymidine phosphorylase function: measurement of plasma thymidine (and deoxyuridine) and thymidine phosphorylase activity. Methods Mol. Biol. 837: 121-133. Available online Dec. 20, 2011.
Nishino, et al. (Jan. 29, 1999). Thymidine phosphorylase gene mutations in MNGIE, a human mitochondrial disorder. Science 283:689-692.
Ronchi, et al. (Jul. 30, 2012). Next-generation sequencing reveals DGUOK mutations in adult patients with mitochondrial DNA multiple deletions. Brain 135:3404-3415.
Sarzi, et al. (Jul. 6, 2007) Twinkle helicase (PEO1) gene mutation caused mitochondrial DNA depletion. Ann. Neurol. 62: 579-587.
Spelbrink, et al. (Jul. 2001). Human mitochondrial DNA deletions associated with mutations in the gene encoding Twinkle, a phage T7 gene 4-like protein localized in mitochondria. Nature Genet. 28:223-231.
Tyynismaa, et al. (Aug. 14, 2009). A heterozygous truncating mutation in RRM2B causes autosomal-dominant progressive external ophthalmoplegia with multiple mtDNA deletions. Am. J. Hum. Genet. 85: 290-295.
Van Goethem, et al. (Jul. 2001) Mutation of POLG is associated with progressive external ophthalmoplegia characterized by mtDNA deletions. Nature Genet. 28:211-212.
Akman, et al. (May 6, 2008) Thymidine kinase 2 (H126N) knock in mice show the essential role of balanced deoxynucleotide pools for mitochondrial DNA maintenance. Hum Mol Genet 17:2433-2440.
Alston, et al. (Dec. 3, 2013) Late-onset respiratory failure due to TK2 mutations causing multiple mtDNA deletions. Neurology. 81:2051-3.
Bartesaghi, et al. (Jan. 26, 2010) Loss of thymidine kinase 2 alters neuronal bioenergetics and leads to neurodegeneration. Hum Mol Genet. 19:1669-77.
Blakely, et al. (Apr. 14, 2008) Novel mutations in the TK2 gene associated with fatal mitochondrial DNA depletion myopathy. Neuromuscular Disorders 18:557-560.
Bourdon, et al. (May 7, 2007) Mutation of RRM2B, encoding p53-controlled ribonucleotide reductase (p53R2), causes severe mitochondrial DNA depletion. Nat Genet 39: 776-780.
Carrozzo, et al. (Jan. 30, 2003) Mutation analysis in 16 patients with mtDNA depletion. Hum Mutat 21:453-454.
Chanprasert, et al. (Jul. 10, 2013) Molecular and clinical characterization of the myopathic form of mitochondrial DNA depletion syndrome caused by mutations in the thymidine kinase (TK2) gene. Mol Genet Metab. 110:153-61.
Chanprasert, et al. (Dec. 6, 2012) TK2-Related Mitochondrial DNA Depletion Syndrome, Myopathic Form. GeneReviews® Internet.
Collins, et al. (Aug. 4, 2009) Progressive myofiber loss with extensive fibro-fatty replacement in a child with mitochondrial DNA depletion syndrome and novel thymidine kinase 2 gene mutations. Neuromuscular Disorders 19:784-787.

Copeland (Mar. 21, 2008) Inherited mitochondrial diseases of DNA replication. Ann. Rev. Med. 59:131-146.
DiMauro, et al. (Feb. 20, 1987) Cytochrome c oxidase deficiency in Leigh syndrome. Ann Neurol 22: 498-506.
DiMauro, Schon. (Jul. 1, 2003) Mitochondrial respiratory-chain diseases. N Engl J Med 348:2656-2668.
DiMauro, Hirano. (2005) Mitochondrial encephalomyopathies: an update. Neuromuscul Disord 15:276-286. Accepted Dec. 10, 2004.
Dorado, et al. (2011) Onset and organ specificity of Tk2 deficiency depends on Tk1 down-regulation and transcriptional compensation. Hum Mol Genet. 20:155-64. Accepted Oct. 6, 2010.
Elpeleg, et al. (Apr. 7, 2005) Deficiency of the ADP-forming succinyl-CoA synthase activity is associated with encephalomyopathy and mitochondrial DNA depletion. Am J Hum Genet 76: 1081-1086.
Ferraro, et al. (2010) Quantitation of cellular deoxynucleoside triphosphates. Nucleic Acids Research 38: e85. Accepted Nov. 18, 2009.
Galbiati, et al. (2006) New mutations in TK2 gene associated with mitochondrial DNA depletion. Pediatr Neurol 34: 177-185. Accepted Jul. 11, 2005.
Garone, et al. (Sep. 10, 2012). MPV17 Mutations Causing Adult-Onset Multisystemic Disorder With Multiple Mitochondrial DNA Deletions. Arch Neurol 69:1648-1651.
Gotz, et al. (Sep. 3, 2008) Thymidine kinase 2 defects can cause multi-tissue mtDNA depletion syndrome. Brain 131:2841-2850.
Hirano, et al. (Dec. 2001) Defects of intergenomic communication: autosomal disorders that cause multiple deletions and depletion of mitochondrial DNA. Semin Cell Develop Biol 12:417-427.
Leshinsky-Silver, et al. (2008) A defect in the thymidine kinase 2 gene causing isolated mitochondrial myopathy without mtDNA depletion. Eur J Paediatr Neurol 12:309-13. Accepted Sep. 2, 2007.
Lesko, et al. (2010) Two novel mutations in thymidine kinase-2 cause early onset fatal encephalomyopathy and severe mtDNA depletion. Neuromuscul Disord 20:198-203. Accepted Nov. 25, 2009.
Lopez, et al. (2009) Unbalanced deoxynucleotide pools cause mitochondrial DNA instability in thymidine phosphorylase deficient mice. Hum Mol Genet 18: 714-722. Accepted Nov. 19, 2008.
Mancuso, et al. (Jul. 2003) Mitochondrial myopathy of childhood associated with mitochondrial DNA depletion and a homozygous mutation (T77M) in the TK2 gene. Arch Neurol. 60:1007-9.
Mancuso, et al. (Jun. 20, 2002) Mitochondrial DNA depletion: mutations in thymidine kinase gene with myopathy and SMA. Neurology. 59:1197-202.
Mandel, et al. (Nov. 2001) The deoxyguanosine kinase gene is mutated in individuals with depleted hepatocerebral mitochondrial DNA. Nat Genet 29: 337-341.
Martí, et al. (Apr. 8, 2010) Hearing loss in a patient with the myopathic form of mitochondrial DNA depletion syndrome and a novel mutation in the TK2 gene. Pediatr Res. 68:151-4.
Martí, et al. (2012) Measurement of mitochondrial dNTP pools. Methods Mol Biol 837: 135-148. Dec. 20, 2011.
Naviaux, Nguyen. (Feb. 4, 2004) POLG mutations associated with Alpers' syndrome and mitochondrial DNA depletion. Ann Neurol 55: 706-712.
Oskoui, et al. (Aug. 2006) Clinical spectrum of mitochondrial DNA depletion due to mutations in the thymidine kinase 2 gene. Arch Neurol 63:1122-1126.
Ostergaard, et al. (Apr. 26, 2007) Deficiency of the alpha subunit of succinate-coenzyme A ligase causes fatal infantile lactic acidosis with mitochondrial DNA depletion. Am J Hum Genet 81: 383-387.
Paradas, et al. (2012) TK2 mutation presenting as indolent myopathy. Neurology 29:504-506. Jan. 9, 2013.
Roos, et al. (May 20, 2014) Mitochondrial DNA depletion in single fibers in a patient with novel TK2 mutations. Neuromuscul Disord. 24:713-20.
Saada, et al. (Oct. 22, 2001) Mutant mitochondrial thymidine kinase in mitochondrial DNA depletion myopathy. Nat Genet 29:342-344.
Saada, et al. (Aug. 7, 2003) Mitochondrial deoxyribonucleoside triphosphate pools in thymidine kinase 2 deficiency. Biochem Biophys Res Commun 310:963-966.

(56) References Cited

OTHER PUBLICATIONS

Spinazzola, et al. (Apr. 2, 2006) MPV17 encodes an inner mitochondrial membrane protein and is mutated in infantile hepatic mitochondrial DNA depletion. Nat Genet 38: 570-575.

Tulinius, et al. (Mar. 6, 2005) Novel mutations in the thymidine kinase 2 gene (TK2) associated with fatal mitochondrial myopathy and mitochondrial DNA depletion. Neuromuscul Disord. 15:412-415.

Tyynismaa, et al. (2012) Thymidine kinase 2 mutations in autosomal recessive progressive exgternal ophthalmoplegia with multiple mitochondrial DNA deletions. Hum Mol Genet 21:66-75. Accepted Sep. 19, 2011.

Vilà, et al. (Apr. 2003) Reversion of mtDNA depletion in a patient with TK2 deficiency. Neurology 60:1203-1205.

Wang, et al. (2005) Molecular insight into mitochondrial DNA depletion syndrome in two patients with novel mutations in the deoxyguanosine kinase and thymidine kinase 2 genes. Mol Genet Metab. 84:75-82. Available online Nov. 11, 2004.

Garonoe et al., "Deoxypyrimidine monophosphate bypass therapy for thymidine kinase 2 deficiency". EMBO Mol Med Jun. 26, 2014 vol. 6 No. 8 pp. 1016-1027. Especially abstract, p. 1016 col. 2, p. 1017 col. 1 para 2, para 2, p. 1024 col. 1 para 1, p. 1024 col. 1 para 5.

MedChem Express. Tipiracil hydrochloride (online) 2014 [retrieved Oct. 26, 2016] Available on the internet: <ULR: https://www.medchemexpress.com/Tipiracilhydrochloride.html?gclid=CjOKEQjwqMHABRDV16_hqKGDyNIBEiQAN-O9hEkNyE4wSbWnZLDeUwtN_gQ5bhgZHaeJwqW6uzbxVkaAsPf8P8HAQ>. Especially p. 1.

Camara et al. "Feeding the deoxyribonucleoside salvage pathway to rescue mitochondrial DNA". Drug Discov Today Oct. 2013 vol. 18 No. 19-20 pp. 950-957. Especially p. 955 col. 5 para 3-4.

Garone et al., "Clinical and genetic spectrum of mitochondrial meurogastrointestinal encephalomyopathy". Brain Nov. 2011 vol. 134 Pt 11 pp. 3326-3332. Especially p. 3328 col. 1 para 3.

Carver, Jane D. "Dietary nucleotides: cellular immune, intestinal and hepatic system effects." The Journal of nutrition 124.suppl_1 (1994): 144S-148S.

Sonoda, Tomoko, and Masamiti Tatibana. "Metabolic fate of pyrimidines and purines in dietary nucleic acids ingested by mice." Biochimica et Biophysica Acta (BBA)-Nucleic Acids and Protein Synthesis 521.1 (1978): 55-66.

Nogueira, Célia, et al. "Syndromes associated with mitochondrial DNA depletion." Italian journal of pediatrics 40.1 (2014): 1-10.

Cámara, Yolanda, et al. "Feeding the deoxyribonucleoside salvage pathway to rescue mitochondrial DNA." Drug discovery today 18.19-20 (Oct. 2013): 950-957.

https://grantome.com/grant/NIH/P01-HD080642-01-5121, May 31, 2015 publication date asserted by SIPO in counterpart China Divisional Patent Application No. 2023107576092, budget start date of Sep. 30, 2014.

Ramón et al., "Therapy Prospects for Mitochondrial DNA Maintenance Disorders," Int. J. Mol. Sci., Jun. 16, 2021, vol. 22, No. 6447, 35 pages.

Dombi et al., "Nucleoside Supplements as Treatments for Mitochondrial DNA Depletion Syndrome," Front. Cell Dev. Biol., Apr. 2, 2024, vol. 12, No. 1260496, 17 pages.

https://grantome.com/grant/NIH/P01-HD080642-01-5121, likely published in RePORTER on Monday Oct. 6, 2014 according to NIH RePORT Support Team.

* cited by examiner

Figure 7A
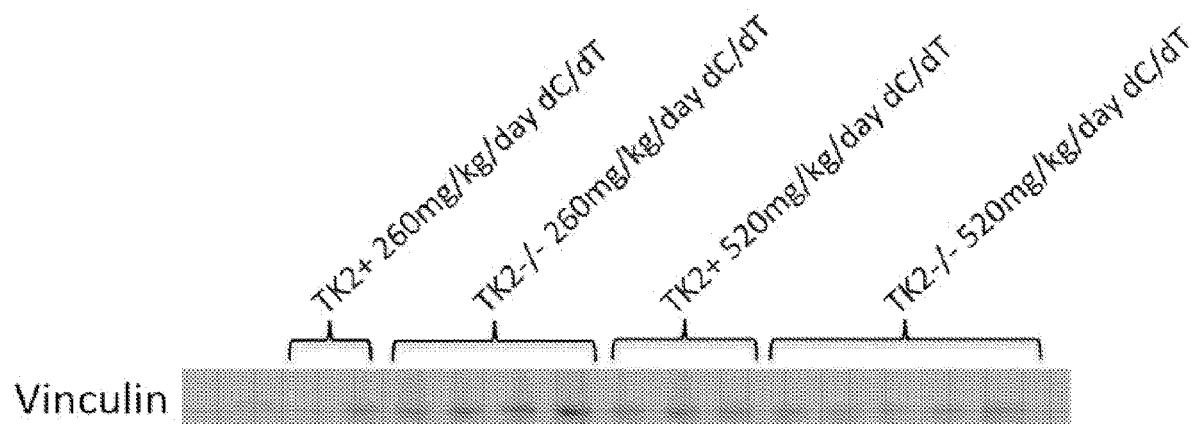
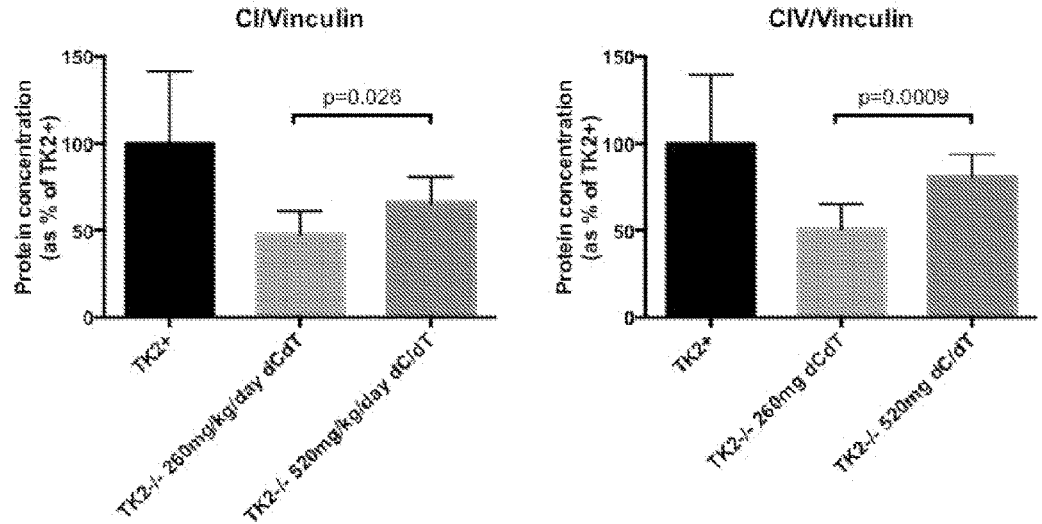
Figure 7B

DEOXYNUCLEOSIDE THERAPY FOR DISEASES CAUSED BY UNBALANCED NUCLEOTIDE POOLS INCLUDING MITOCHONDRIAL DNA DEPLETION SYNDROMES

CROSS-REFERENCE TO RELATED PATENT APPLICATIONS

This application is a divisional of U.S. application Ser. No. 17/242,822 filed Apr. 28, 2021, which is a continuation of U.S. application Ser. No. 16/583,852, filed Sep. 26, 2019, now U.S. Pat. No. 11,110,111, which is a Continuation of U.S. application Ser. No. 15/736,092, filed Dec. 13, 2017, now U.S. Pat. No. 10,471,087, issued Nov. 12, 2019, which is a U.S. National Phase Application under 35 U.S.C. § 371 of International Patent Application No. PCT/US2016/038110, filed Jun. 17, 2016, which claims priority to U.S. Provisional Application No. 62/180,914, filed Jun. 17, 2015, all of which are incorporated by reference, as if expressly set forth in their respective entireties herein.

CROSS-REFERENCE TO RELATED APPLICATIONS

The present application claims priority to U.S. provisional patent application Ser. No. 62/180,194 filed Jun. 17, 2015, which is hereby incorporated by reference.

GOVERNMENT SUPPORT

This invention was made with government support under HD080642 awarded by NIH. The government has certain rights in the invention.

FIELD OF THE INVENTION

The invention relates generally to a pharmacological therapy for a human genetic disease, specifically diseases characterized by unbalanced nucleotide pools, e.g., mitochondrial DNA depletion syndromes, and more specifically, thymidine kinase 2 (TK2) deficiency. The pharmacological therapy involves the administration of at least one deoxynucleoside, or mixtures thereof. For the treatment of TK2 deficiency, the pharmacological therapy involves the administration of either deoxythymidine (dT) or deoxycytidine (dC), or mixtures thereof. This administration of one or more deoxynucleosides is applicable to other disorders of unbalanced nucleoside pools, especially those found in mitochondrial DNA depletion syndrome.

BACKGROUND OF THE INVENTION

Mitochondrial diseases are clinically heterogeneous diseases due to defects of the mitochondrial respiratory chain (RC) and oxidative phosphorylation, the biochemical pathways that convert energy in electrons into adenosine triphosphate (ATP). The respiratory chain is comprised of four multi-subunit enzymes (complexes 1-IV) that transfer electrons to generate a proton gradient across the inner membrane of mitochondria and the flow of protons through complex V drives ATP synthesis (DiMauro and Schon 2003; DiMauro and Hirano 2005). Coenzyme $Q_{10}$ ($CoQ_{10}$) is an essential molecule that shuttles electrons from complexes I and II to complex III. The respiratory chain is unique in eukaryotic, e.g., mammalian, cells by virtue of being controlled by two genomes, mitochondrial DNA (mtDNA) and nuclear DNA (nDNA). As a consequence, mutations in either genome can cause mitochondrial diseases. Most mitochondrial diseases affect multiple body organs and are typically fatal in childhood or early adult life. There are no proven effective treatments for mitochondrial diseases, only supportive therapies, such as the administration of $CoQ_{10}$ and its analogs to enhance respiratory chain activity and to detoxify reactive oxygen species (ROS) that are toxic by-products of dysfunctional respiratory chain enzymes.

Mitochondrial DNA depletion syndrome (MDS), which is a subgroup of mitochondrial disease, is a frequent cause of severe childhood encephalomyopathy characterized molecularly by reduction of mitochondrial DNA (mtDNA) copy number in tissues and insufficient synthesis of mitochondrial RC complexes (Hirano, et al. 2001). Mutations in several nuclear genes have been identified as causes of infantile MDS, including: TK2, DGUOK, POLG, POLG2, SCLA25A4, MPV17, RRM2B, SUCLA2, SUCLG1, TYMP, OPA1, and C10orf2 (PEO1). (Bourdon, et al. 2007; Copeland 2008; Elpeleg, et al. 2005; Mandel, et al. 2001; Naviaux and Nguyen 2004; Ostergaard, et al. 2007; Saada, et al. 2003; Sarzi, et al. 2007; Spinazzola, et al, 2006). In addition, mutations in these nuclear genes can also cause multiple deletions of mtDNA with or without mtDNA depletion (Béhin, et al. 2012; Garone, et al. 2012; Longley, et al. 2006; Nishino, et al. 1999; Paradas, et al. 2012; Ronchi, et al. 2012; Spelbrink, et al. 2001; Tyynismaa, et al. 2009; Tyynismaa, et al. 2012; Van Goethem, et al. 2001).

One of these genes is TK2, which encodes thymidine kinase (TK2), a mitochondrial enzyme required for the phosphorylation of the pyrimidine nucleosides (thymidine and deoxycytidine) to generate deoxythymidine monophosphate (dTMP) and deoxycytidine monophosphate (dCMP) (Saada, et al. 2001). Mutations in TK2 impair the mitochondrial nucleoside/nucleotide salvage pathways required for synthesis of deoxynucleotide triphosphate (dNTP), the building blocks for mDNA replication and repair.

TK2 deficiency was first described in 2001 by Saada and colleagues (Saada, et al. 2001), in four affected children originating from four different families, who suffered from severe, devastating myopathy. After an uneventful early development, at ages 6-36 months the patients developed hyperCKemia, severe muscle hypotonia with subsequent loss of spontaneous activity. The disease was rapidly progressive and two patients were mechanically ventilated at 3 years, while two other patients were already dead by the time of the report.

After the first description, sixty additional patients have been reported in literature and at least twenty-six further patients have been diagnosed but not reported (Alston, et al. 2013; Bartesaghi, et al. 2010; Béhin, et al. 2012; Blakely, et al. 2008: Carrozzo, et al. 2003; Chanprasert, et al. 2013; Collins, et al. 2009; Galbiati, et al. 2006; Gotz, et al. 2008; Leshinsky-Silver, et al. 2008; Lesko, et al. 2010; Mancuso, et al. 2002; Mancuso, et al. 2003; Marti, et al. 2010; Oskoui, et al. 2006; Paradas, et al. 2012; Roos, et al. 2014; Tulinius, et al. 2005; Tyynismaa, et al. 2012; Vilá, et al. 2003; Wang, et al. 2005), resulting in ninety patients, 53 males and 37 females.

The twenty-six patients recently diagnosed were identified through next-generation DNA sequencing. This large number of newly identified cases suggests that TK2 deficiency is an under diagnosed disorder.

TK2 deficiency manifests a wide clinical and molecular genetic spectrum with the majority of patients manifesting in early childhood with a devastating clinical course, while others have slowly progressive weakness over decades.

Treatment for TK2 deficiency, like most MDS and mitochondrial disorders, has been limited to supportive therapies. While the administration of deoxythymidine monophosphate (dTMP) and deoxycytidine monophosphate (dCMP) improved the conditions of both TK2 knock-in mutant mice and human patients with TK2 deficiency (U.S. application Ser. No. 15/082,207, which is incorporated herein in its entirety), there is still a need for therapeutic intervention for TK2 deficiency.

Additionally, there is a need for treatment for other forms of MDS and other diseases characterized by unbalanced nucleotide pools. For example, several mendelian disorders with mtDNA depletion or multiple deletions, or both are characterized by unbalanced deoxynucleotide triphosphate pools that lead to defects of mtDNA replication. One such disorder, DGUOK mutations impair the intramitochondrial enzyme deoxyguanosine kinase, which normally phosphorylates the deoxypurine nucleosides deoxguanosine and deoxycytidine to generate deoxguanosine monophosphate (dGMP) and deoxycytidine monophosphate (dCMP). Other nuclear genes that disrupt mitochondrial dNTP pools include TYMP, RRM2B, SUCLA2, SUCLG1 and MPV17. Therapies that restore dNTP pool balance would be useful to treat these disorders as well.

SUMMARY OF THE INVENTION

In certain embodiments, the present invention relates to a method of treating a disease or disorder characterized by unbalanced nucleotide pools, comprising administering to a subject in need thereof a therapeutically effective amount of a composition comprising one or more deoxynucleosides.

Diseases or disorders characterized by unbalanced nucleotide pools that can be treated by the method of the current invention include, but are not limited to, those characterized by mutations in the following genes: TK2; DGUOK; TYMP; RRM2B; SUCLA2; SUCLG1; and MPV17.

In a preferred embodiment, the disorder is a mitochondrial DNA depletion syndrome (MDS). In a more preferred embodiment, the MDS includes disorders of a myopathic form characterized by mutations in TK2, an encephalomyopathic form characterized by mutations in SUCLA2, a neurogastrointestinal encephalopathic form characterized by mutations in TYMP, and a hepatopathic form characterized by mutations in DGUOK, POLG, and MPV17. In a most preferred embodiment, the disorder is a thymidine kinase 2 deficiency, characterized by mutation(s) in the TK2 gene.

All mitochondrial DNA depletion syndromes can be treated with the method of the current invention which comprises administering deoxynucleosides. Examples of MDS that can be treated by the method of the current invention include but are not limited to, deficiencies in the: DGUOK gene, encoding deoxyguanosine kinase, dGK; RRM2B gene, encoding p53R2, the p53 inducible small subunit of ribonucleotide reductase, RNR; and TYMP gene, encoding thymidine phosphorylase, TP.

In a preferred embodiment, the deoxynucleoside is either deoxythymidine (dT) or deoxycytidine (dC) or mixtures thereof. Deoxyadenosine (dA) and deoxyguanosine (dG), alone or together, can also be used in the method of the invention. One deoxynucleoside (i.e., dT, dC, dA, or dG) and mixtures of two or more of any of the four deoxynucleosides can be used in the method of the invention.

Preferred dosages of the deoxynucleoside(s) are between about 100 and about 1,000 mg/kg/day, more preferably between about 300 and about 800 mg/kg/day, and most preferably between about 250 and about 600 mg/kg/day. If the composition comprises a single deoxynucleoside, then the dosages are of the single deoxynucleoside. If the composition comprises more than one deoxynucleoside, the dosages can be of each deoxynucleoside or of the total deoxynucleosides in the composition.

Administration of the deoxynucleoside(s) can be once daily, twice daily, three times daily, four times daily, five times daily, up to six times daily, preferably at regular intervals.

Preferred methods of administration are oral, intrathecal, intravenous, and enteral.

Administration of the deoxynucleoside(s) should begin as soon as the disorder characterized by unbalanced nucleotide pools, e.g., MDS, is suspected and continue throughout the life of the patient. Test for the diagnosis of such disorders including TK2 deficiency are known in the art.

BRIEF DESCRIPTION OF THE DRAWINGS

For the purpose of illustrating the invention, there are depicted in drawings certain embodiments of the invention. However, the invention is not limited to the precise arrangements and instrumentalities of the embodiments depicted in the drawings.

Figure 1:
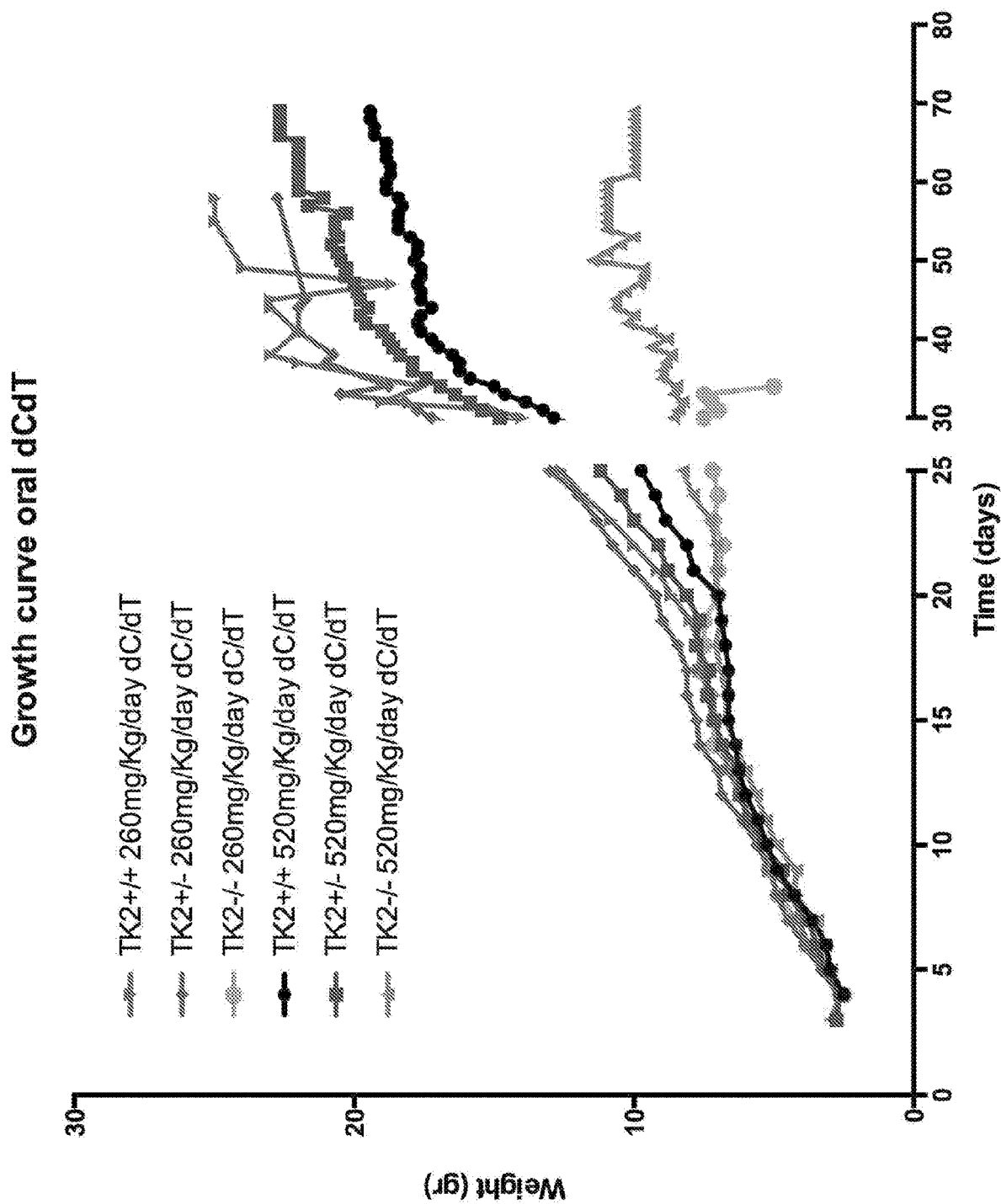
FIG. 1 depicts a growth curve of wild type ($Tk2^{+/+}$ and $Tk2^{+/-}$), and $Tk2^{-/-}$ mice treated with 260 mg/kg/day or 520 mg/kg/day of deoxycytidine (dC) and deoxythymidine (dT) from postnatal day 4. Each symbol represents the mean of weight at each time-point. N of each group is indicated in figure.

FIG. 7A is an immunoblot of respiratory chain proteins in wild type mice treated with 260 mg/kg/day or 520 mg/kg/day of deoxycytidine (dC) and deoxythymidine (dT), and Tk2$^{-/-}$ mice treated with 260 mg/kg/day or 520 mg/kg/day of deoxycytidine (dC) and deoxythymidine (dT) at 29 days postnatal. FIG. 7B are graphs showing the RCE levels normalized to complex II, represented as percent of the RCE levels in TK2$^{+/+}$ mice. p-values were assessed by Mann-Whitney tests.

Abbreviations: CS=citrate synthase; CI=NADH-dehydrogenase; CII=succinate dehydrogenase; CIII=cytochrome c reductase; CIV=cytochrome c oxidase (COX); CI+III=NADH-cytochrome c reductase; CII+III=succinate dehydrogenase-cytochrome c reductase.

DETAILED DESCRIPTION OF THE INVENTION

The current invention is based upon the surprising discovery that mitochondrial DNA depletion syndromes, including TK2 deficiency, can be treated with deoxynucleosides. As shown by the results herein, the administration of deoxynucleosides greatly improved the condition in both a mouse model of TK2 deficiency and human patients with TK2 deficiency.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means mammals. Mammals include canines, felines, rodents, bovine, equines, porcines, ovines, and primates. Thus, the invention can be used in veterinary medicine, e.g., to treat companion animals, farm animals, laboratory animals in zoological parks, and animals in the wild. The invention is particularly desirable for human medical applications The term "patient" as used in this application means a human subject. In some embodiments of the present invention, the "patient" is known or suspected of having a disease or disorder characterized by unbalanced nucleotide pools, mitochondrial disease, mitochondrial DNA depletion syndrome, or TK2 deficiency.

The phrase "therapeutically effective amount" is used herein to mean an amount sufficient to cause an improvement in a clinically significant condition in the subject, or delays or minimizes or mitigates one or more symptoms associated with the disease or disorder, or results in a desired beneficial change of physiology in the subject.

The terms "treat", "treatment", and the like refer to a means to slow down, relieve, ameliorate or alleviate at least one of the symptoms of the disease or disorder, or reverse the disease or disorder after its onset.

The terms "prevent", "prevention", and the like refer to acting prior to overt disease or disorder onset, to prevent the disease or disorder from developing or minimize the extent of the disease or disorder, or slow its course of development.

The term "in need thereof" would be a subject known or suspected of having or being at risk of having a disease or disorder characterized by unbalanced nucleotide pools, mitochondrial disease, mitochondrial DNA depletion syndrome, or TK2 deficiency.

The term "agent" as used herein means a substance that produces or is capable of producing an effect and would include, but is not limited to, chemicals, pharmaceuticals, biologics, small organic molecules, antibodies, nucleic acids, peptides, and proteins.

The term "deoxynucleoside" as used herein means deoxythymidine or dT, deoxycytidine or dC, deoxyadenosine or dA, and deoxyguanosine or dG. The full length name and common abbreviation for each will be used interchangeably. Such deoxynucleosides also include physiologically functional derivatives of the deoxynucleosides.

As used herein, the term "physiologically functional derivative" refers to a compound (e.g, a drug precursor) that is transformed in vivo to yield a deoxynucleoside. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the *A.C.S. Symposium Series*, and in Bioreversible Carriers in Drug Design, ed. Edward B. Roche, American Pharmaceutical Association and Pergamon Press, 1987.

As used herein "an adverse effect" is an unwanted reaction caused by the administration of a drug. In most cases, the administration of the deoxynucleosides caused no adverse effects. The most expected adverse effect would be a minor gastrointestinal intolerance.

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

Administration of Deoxynucleosides for the Treatment of Mitochonodrial DNA Depletion Syndrome Mitochondrial DNA (mtDNA) depletion syndrome (MDS) comprises several severe autosomal diseases characterized by a reduction in mtDNA copy number in affected tissues. Most of the MDS causative nuclear genes encode proteins that belong to the mtDNA replication machinery or are involved in deoxyribonucleoside triphosphate (dNTP) metabolism.

One form of MDS is thymidine kinase deficiency or TK2. TK2 encoded by the nuclear gene, TK2, is a mitochondrial matrix protein that phosphorylates thymidine and deoxycytidine nucleosides to generate deoxythymidine monophosphate (dTMP) and deoxycytidine monophosphate (dCMP), which in turn, are converted to deoxynucleotide triphosphates (dNTPs) required for mitochondrial DNA synthesis. As discussed in the background section, autosomal recessive TK2 mutations cause devastating neuromuscular weakness with severe depletion of mitochondrial DNA (mtDNA) in infants and children, as well as progressive external ophthalmoplegia with mtDNA multiple deletions in adults. Many patients cannot walk and require some type of mechanical ventilation and feeding tube. The central nervous system is variably involved in these disorders, with symptoms that include seizures, encephalopathy, cognitive impairment, and hearing loss. Less than 7% of patients live more than 42 years.

Based on clinical and molecular genetics findings of patients thus diagnosed, three disease presentations were identified: i) infantile-onset (≤1 year-old) myopathy with onset of weakness in the first year of life with severe mtDNA depletion and early mortality: ii) childhood-onset (>1-11 years-old) myopathy with severe mtDNA depletion; and iii) late-onset myopathy (≥12 years-old) with mild weakness at onset and slow progression to loss of ambulation, respiratory insufficiency, or both, often with chronic progressive external ophthalmoparesis in adolescence or adulthood in association with mtDNA multiple deletions, reduced mtDNA copy number, or both. See generally Garone, et al., (2016) in preparation.

Attempts to study the pathogenesis and test therapies for TK2 deficiency using cultured fibroblasts from patients have been unsuccessful, because the replicating cells failed to manifest mtDNA depletion. In contrast, a homozygous Tk2 H126N knock-in mutant (Tk2$^{-/-}$) mouse model, manifests a phenotype that is strikingly similar to the human infantile encephalomyopathy caused by TK2 mutations, characterized by onset at age 10 days with decreased ambulation, unstable gait, coarse tremor, growth retardation, and depletion of mitochondrial DNA (mtDNA) progressing rapidly to early death at age 14 to 16 days, which is a time period analogous to the human infantile-onset disease (Akman, et al. 2008; Dorado, et al. 2011).

The studies set forth herein with Tk2 knock-in mice have shown the administration of oral dC/dT prolonged delayed the onset of clinical symptoms of TK2 deficiency and prolonged the lives of the mice by two- to three-fold (Example 2).

Additional experiments showed tissue-specific effects. Measurement of the dNTP pool levels in mitochondria extracts showed that dCTP was rescued in brain and dTTP was rescued in liver (Example 3). Measurement of mtDNA depletion showed both dCMP+dTMP and dC+dT therapies rescued the mtDNA copy number in liver, muscle and tissue (Example 4). It was previously speculated that formation of the blood brain barrier might be compromising the treatment bioavailability in brain. Nevertheless, HPLC measurements showed that catalytic products of these compounds were found in higher concentrations after both nucleotides monophosphates and deoxynucleosides treatment, suggesting that they are capable of crossing the blood brain barrier. mtDNA depletion measurements also showed a completely rescue of mtDNA copy number in intestine.

Thus, the experiments set forth herein using the mouse model of Tk2 deficiency show the administration of deoxynucleosides to be effective and safe for the treatment of the disease. Additionally, as shown in Example 5, the administration of dT and dC greatly improved the symptoms of TK2 deficiency in patients.

Thus, the present invention includes the administration of at least one deoxynucleoside to a patient in need thereof. In one embodiment, the present invention includes the administration of at least one deoxypyrimidine. In a further embodiment, the deoxypyrimidine is chosen from dC, dT and mixtures thereof. In yet another embodiment, the present invention includes the administration of at least one deoxypurine. In a further embodiment, the deoxypurine is chosen from dA, dG, and mixtures thereof.

Patients who would benefit from the administration of deoxynucleosides would be those diagnosed with TK2 deficiency. In these patients, at least one deoxypyrimidine, dC or dT, or mixtures thereof would be administered.

A parallel defect of deoxyguanosine kinase (dGK), due to autosomal recessive mutations in DGUOK with deficiencies in dGMP and dAMP, causes mtDNA depletion typically manifesting as early childhood-onset hepatocerebral disease (Mandel, et al. 2001). These patients would benefit from the administration of at least one deoxypurine, dG or dA, or mixtures thereof.

Other forms of MDS as well as other disorders related to unbalanced nucleotide pools can be treated by the administration of specific deoxynucleosides, i.e., dA, dG, dC, or dT, or mixtures thereof. These disorders would include but are not limited to deficiencies related to RRM2B (encoding p53R2, the p53 inducible small subunit of ribonucleotide reductase, RNR) and mutations in TYMP (encoding thymidine phosphorylase, TP) which cause mitochondrial neurogastrointestinal encephalomyopathy (MNGIE). Additional nuclear genes that disrupt mitochondrial dNTP pools include but are not limited to SUCLA2, SUCLG1 and MPV17. Disorders related to these genes can also be treated by the administration of one or more deoxynucleosides.

Additionally, as the mechanisms of other forms of MDS and other disorders become elucidated, the proper deoxynucleoside(s) for treatment can be determined by the skilled practitioner.

Patients that exhibit the phenotype discussed above for TK2 deficiency including the most typical presentation of progressive muscle disease characterized by generalized hypotonia, proximal muscle weakness, loss of previously acquired motor skills, poor feeding, and respiratory difficulties, can be tested to definitively diagnose the disease.

If the clinical presentation is highly suspicious for mtDNA depletion syndrome, molecular genetic testing using a panel of genes known to cause mtDNA depletion syndrome should be performed (Chanprasert, et al. 2012). The TK2 gene is the only gene in which mutations are known to cause TK2-related mitochondrial DNA depletion syndrome. This testing can include a sequence analysis of the entire coding and exon/intron junction regions of TK2 for sequence variants and deletion/duplication. If compound heterozygous or homozygous deleterious mutations are identified in the sequence analysis, the diagnosis of TK2 deficiency is confirmed, and thus, the subject would benefit from the deoxynucleoside therapy. If sequence analysis does not identify two compound heterozygous or homozygous deleterious mutations, deletion/duplication analysis should be considered to determine and/or confirm a TK2 deficiency diagnosis.

Further tests to determine and/or confirm a TK2 deficiency diagnosis may include testing serum creatine kinase (CK) concentration, electromyography, histopathology on skeletal muscle, mitochondrial DNA (mtDNA) content (copy number), and electron transport chain (ETC) activity in skeletal muscle. If one or more of the following is found in these tests, the TK2 deficiency is determined and/or confirmed. Elevated CK concentration as compared to healthy controls can indicate TK2 deficiency. A skeletal muscle biopsy can be performed, and then a mtDNA content analysis in skeletal muscle performed. If the skeletal muscle biopsy shows prominent variance in fiber size, variable sarcoplasmic vacuoles, variable increased connective tissue, and ragged red fibers as well as increased succinate dehydrogenase (SDH) activity and low to absent cytochrome c oxidase (COX) activity, and mtDNA copy number is severely reduced (typically less than 20% of age- and tissue-matched healthy controls), a diagnosis of TK2 deficiency can be determined and/or confirmed (Chanprasert, et al. 2012).

Additionally, TK2 deficiency is inherited in an autosomal recessive manner. Thus, a sibling of an affected patient can be tested as early as possible after birth to diagnose the disease.

In all of these examples, deoxynucleoside therapy should be started as soon as possible after a diagnosis of TK2 deficiency.

Pharmaceutical Compositions, Methods of Administration, and Dosing

The present invention encompasses the administration of deoxynucleosides, more specifically one or more deoxynucleosides.

Most preferred methods of administration are oral, intrathecal and parental including intravenous. The deoxynucleosides must be in the appropriate form for administration of choice.

Deoxynucleosides are easily dissolved in liquid are easily dissolved in liquid (such as water, formula or milk) whereas the free acid form does not readily dissolve in liquid.

Such pharmaceutical compositions comprising one of more deoxynucleosides for administration may comprise a therapeutically effective amount of the deoxynucleosides and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

Oral administration is a preferred method of administration. The deoxynucleosides can be added to any form of liquid a patient would consume including but not limited to, milk, both cow's and human breast, infant formula, and water.

Additionally, pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

In order to overcome any issue of the deoxynucleosides crossing the blood/brain barrier, intrathecal administration is a further preferred form of administration (Galbiati, et al. 2006; Gotz, et al. 2008). Intrathecal administration involves injection of the drug into the spinal canal, more specifically the subarachnoid space such that it reaches the cerebrospinal fluid. This method is commonly used for spinal anesthesia, chemotherapy, and pain medication. Intrathecal administration can be performed by lumbar puncture (bolus injection) or by a port-catheter system (bolus or infusion). The catheter is most commonly inserted between the laminae of the lumbar vertebrae and the tip is threaded up the thecal space to the desired level (generally L3-L4). Intrathecal formulations most commonly use water, and saline as excipients but EDTA and lipids have been used as well.

A further preferred form of administration is parenteral including intravenous administration. Pharmaceutical compositions adapted for parenteral administration, including intravenous administration, include aqueous and non-aqueous sterile injectable solutions or suspensions, which may contain anti-oxidants, buffers, bacteriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Additionally, since some patients may be receiving enteral nutrition by the time the deoxynucleoside treatment begins, the dNs can be administered through a gastronomy feeding tube or other enteral nutrition means.

Further methods of administration include mucosal, such as nasal, sublingual, vaginal, buccal, or rectal; or transdermal administration to a subject.

Pharmaceutical compositions adapted for nasal and pulmonary administration may comprise solid carriers such as powders, which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided as pessaries, tampons, creams, gels, pastes, foams or spray formulations.

Pharmaceutical compositions adapted for transdermal administration may be provided as discrete patches intended to remain in intimate contact with the epidermis of the recipient over a prolonged period of time.

The deoxynucleoside therapy comprises the administration of one or more deoxynucleosides chosen from the group consisting of deoxythymidine (dT), deoxycytidine (dC), deoxyadenosine (dA) and deoxyguanosine (dG).

A skilled practitioner can determine which deoxynucleosides are beneficial based upon the deficiency. It is also within the skill of the art for the practitioner to determine if mixtures of the deoxynucleosides should be administered and in what ratio. If two deoxynucleosides are to be administered, they can be in a ratio of 50/50 of each deoxynucleoside, e.g., dC and dT, or in ratios of about 5/95, 10/90, 15/85, 20/80, 25/75, 30/70, 35/65, 40/60, 45/55, 55/45, 60/40, 65/35, 70/30, 75/25, 80/20, 85/15, 90/10, and 95/5.

By way of example, dT and dC are administered in mixture of equal amounts for TK2 deficiency.

Selection of a therapeutically effective dose will be determined by the skilled artisan considering several factors, which will be known to one of ordinary skill in the art. Such factors include the particular form of the deoxynucleoside, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

A preferred dose ranges from about 100 mg/kg/day to about 1,000 mg/kg/day. A further preferred dose ranges from about 200 mg/kg/day to about 800 mg/kg/day. A further preferred dose ranges from about 250 mg/kg/day to about 400 mg/kg/day. These dosage amounts are of individual deoxynucleosides or of a composition with a mixture of more than one deoxynucleosides, e.g., dT and dC. For example, a dose can comprise 400 mg/kg/day of dT alone. In a further example, a dose can comprise a mixture of 200 mg/kg/day of dT and 200 mg/kg/day of dC. In a further example, a dose can comprise 400 mg/kg/day of a mixture of dT and dC.

Administration of the deoxynucleosides can be once a day, twice a day, three times a day, four times a day, five times a day, up to six times a day, preferably at regular intervals. For example, when the deoxynucleosides are administered four times daily, doses would be at 8:00 AM, 12:00 PM, 4:00 PM, and 8:00 PM.

Doses can also be lowered if being administered intravenously or intrathecally. Preferred dose ranges for such administration are from about 50 mg/kg/day to about 500 mg/kg/day.

As shown in Example 5, doses can be adjusted to optimize the effects in the subject. For example, the deoxynucleosides can be administered at 100 mg/kg/day to start, and then increased over time to 200 mg/kg/day, to 400 mg/kg/day, to 800 mg/kg/day, up to 1000 mg/kg/day, depending upon the subject's response and tolerability.

A subject can be monitored for improvement of their condition prior to increasing the dosage. A subject's response to the therapeutic administration of the deoxynucleosides can be monitored by observing a subject's muscle strength and control, and mobility as well as changes in height and weight. If one or more of these parameters increase after the administration, the treatment can be continued. If one or more of these parameters stays the same or decreases, the dosage of the deoxynucleosides can be increased.

As shown in the Examples, the deoxynucleosides are well tolerated. Any observed adverse effects were minor and were mostly diarrhea, abdominal bloating and other gastrointestinal manifestations. A subject can also be monitored for any adverse effects, such as gastrointestinal intolerance, e.g., diarrhea. If one or more adverse effects are observed after administration, then the dosage can be decreased. If no such adverse effects are observed, then the dosage can be increased. Additionally, once a dosage is decreased due to the observation of an adverse effect, and the adverse effect is no longer observed, the dosage can be increased.

The deoxynucleosides can also be co-administered with other agents. Such agents would include therapeutic agents for treating the symptoms of the particular form of MDS. In particular, for TK2 deficiency, the dT and dC can be co-administered with an inhibitor of ubiquitous nucleoside catabolic enzymes, including but not limited to enzyme inhibitors such as tetrahydrouridine (inhibitor of cytidine deaminase) and immucillin H (inhibitor of purine nucleoside phosphorylase) and tipiracil (inhibitor of thymidine phosphorylase). Such inhibitors are known and used in the treatment of some cancers.

EXAMPLES

The present invention may be better understood by reference to the following non-limiting examples, which are presented in order to more fully illustrate the preferred embodiments of the invention. They should in no way be construed to limit the broad scope of the invention.

Example 1—Materials and Methods

Mouse Model of TK2 Deficiency

A homozygous Tk2 H126N knock-in mutant (Tk2$^{-/-}$) mouse that manifests a phenotype strikingly similar to the human infantile encephalomyopathy has been previously reported (Akman, et al. 2008). Between postnatal day 10 and 13, Tk2$^{-/-}$ mice rapidly develop fatal encephalomyopathy characterized by decreased ambulation, unstable gait, coarse tremor, growth retardation, and rapid progression to early death at age 14 to 16 days. Molecular and biochemical analyses of the mouse model demonstrated that the pathogenesis of the disease is due to loss of enzyme activity and ensuing dNTP pool imbalances with decreased dTTP levels in brain and both dTTP and dCTP levels in liver, which, in turn, produces mtDNA depletion and defects of respiratory chain enzymes containing mtDNA-encoded subunits, most prominently in the brain and spinal cord.

All experiments were performed according to a protocol approved by the Institutional Animal Care and Use Committee of the Columbia University Medical Center, and were consistent with the National Institutes of Health *Guide for the Care and Use of Laboratory Animals*. Mice were housed and bred according to international standard conditions, with a 12-hour light, 12-hour dark cycle, and sacrificed at 4, 13, and 29 days of age.

Organs (brain, spinal cord, liver, heart, kidney, quadriceps muscle, lung, and gastrointestinal tract) were removed and either frozen in the liquid phase of isopentane, pre-cooled near its freezing point (−160° C.) with dry ice or fixed in 10% neutral buffered formalin and embedded in paraffin using standard procedures. Paraffin embedded tissue were then stained with hematoxylin and eosin (H&E) for morphological study or processed for immunostaining studies with GFAP, COX I, or complex I subunit as detailed described in the supplemental procedures. Both heterozygous and homozygous wild type mice were considered as control group (Tk2$^+$) since no clinical and biochemical difference were previously described (Akman, et al. 2008; Dorado, et al. 2011).

Treatment Administration and Experimental Plan

Deoxycytidine (dC) and deoxythymidine (dT) were administered in 50 µl of Esbilac milk formula for small pets (Pet-Ag) by daily oral gavage to Tk2 H126N knockin mice (Tk2$^{-/-}$) and aged matched control wild-type (Tk2$^f$) using 2 doses, 260 mg/kg/day and 520 mg/kg/day, from post-natal day 4 to 29 days. At age 21 days, mice were separated from the mother and the treatment was continued by administration of dC and dT in drinking water using equimolar doses respectively of 1.6 mM and 3.2 mM. A negative control group of untreated Tk2 mutant and control wild-type mice were weighed and observed closely for comparison.

Phenotype Assessment

Body weight was assessed daily, since it has been previously observed that incapacity of gaining weight is the first sign of disease (Akman, et al. 2008).

To define the degree of safety and efficacy of dT/dC, survival time, age-at-onset of disease, type and severity of symptoms, occurrence of side effects, and proportion of treatment termination due to adverse events in treated and untreated Tk2 mice were compared. General behavior, survival time, and body weights of the mice were assessed daily beginning at postnatal day 4.

dNTP Pool by Polymerase Extension Assay

Tissues were homogenized on ice in 10 volumes (w/v) of cold MTSE buffer (210 mM mannitol, 70 mM sucrose, 10 mM Tris-HCl pH 7.5, 0.2 mM EGTA, 0.5% BSA) and centrifuged at 1000 g for 5 minutes at 4° C., followed by three centrifugations at 13,000 g for 2 minutes at 4° C. Supernatant was precipitated with 60% methanol, kept 2 hours at −80° C., boiled 3 minutes, stored at −80° C. (from 1 hour to overnight) and centrifuged at 20,800 g for 10 minutes at 4° C. Supernatants were evaporated until dry and pellet was resuspended in 65 µl of water and stored at −80° C. until analysed. To minimize ribonucleotide interference, total dNTP pools were determined as reported (Ferraro, et al. 2010; Marti, et al. 2012a). Briefly, 20 µl volume reactions was generated by mixing 5 µl of sample or standard dNTP with 15 µl of reaction buffer [0.025 U/ml ThermoSequenase DNA polymerase (GE Healthcare, Piscataway, NJ, USA) or Taq polymerase (Life Technologies, NY, USA), 0.75 M 3H-dTTP or 3H-dATP (Moravek Biochemicals), 0.25 µM specific oligonucleotide, 40 mM Tris-HCl, pH 7.5, 10 mM MgCl2, 5 mM DTT]. After 60 minutes at 48° C., 18 ml of reaction were spotted on Whatman DE81 filters, air dried and washed three times for 10 minutes with 5% Na2HPO4, once in distilled water and once in absolute ethanol. The retained radioactivity was determined by scintillation counting.

Nucleosides Measurements by HPLC

Deoxythymidine (dT), deoxyuridine (dU), uracil (U) and thymine (T) levels were assessed by a gradient-elution HPLC method as described previously (Lopez, et al. 2009; Marti, et al. 2012b), with minor modifications. Briefly, deproteinized samples were injected into an Alliance HPLC system (Waters Corporation) with an Alltima C18NUC reversed-phase column (Alltech) at a constant flow rate of 1.5 ml/min (except where indicated) using four buffers: eluent A (20 mM potassium phosphate, pH 5.6), eluent B (water) and eluent C (methanol). Samples were eluted over 60 minutes with a gradient as follows: 0-5 min, 100% eluent A; 5-25 min, 100-71% eluent A, 29% eluent B; 25-26 min, 0-100% eluent C; 26-30 min, 100% eluent C; 30-31 min, 0-100% eluent B; 31-35 min, 100% eluent B (1.5-2 ml/min); 35-45 min, 100% eluent B (2 ml/min); 45-46 min, 100% eluent B (2-1.5 ml/min); 46-47 min, 0-100% eluent C; 47-50 min, 100% eluent C; 50-51 min, 0-100% eluent A; and 51-60 min, 100% eluent A.

Absorbance of the eluates was monitored at 267 nm and dThd and dUrd peaks were quantified by comparing their peak areas with a calibration curve obtained with aqueous standards. For definitive identification of deoxythymidine, deoxyuridine, uracil, and thymine peaks for each sample, a second aliquot was treated with excess of purified *E. coli* TP (Sigma) to specifically eliminate dT and dU. The detection limit of this method is 0.05 mmol/l for all nucleosides. Results were expressed as nmol/mg of protein.

RT-qPCR: Mitochondrial DNA Quantification

Real-time PCR was performed with the primers and probes for murine COX I gene (mtDNA) and mouse glyceraldehyde-3-phosphate dehydrogenase (GAPDH, nDNA) (Applied Biosystems, Invitrogen, Foster City, CA, USA) as described as described using ddCt method in a Step One Plus Real Time PCR System (Applied Biosystems) (Dorado, et al. 2011). MtDNA values were normalized to nDNA values and expressed as percent relative to wild-type (100%).

Mitochondrial Respiratory Chain Protein Levels

Thirty micrograms of whole brain cerebrum or cerebellum extracts were electrophoresed in an SDS-12% PAGE gel, transferred to Immun-Blot™ PVDF membranes (Biorad, Hercules, CA, USA) and probed with MitoProfile® Total OXPHOS Rodent WB Antibody Cocktail of antibodies (MitoSciences, Eugene, OR, USA). Protein-antibody interaction was detected with peroxidase-conjugated mouse antimouse IgG antibody (Sigma-Aldrich, St Louis, MO, USA), using Amersham™ ECL Plus western blotting detection system (GE Healthcare Life Sciences, UK). Quantification of proteins was carried out using NIH ImageJ 1.37V software. Average gray value was calculated within selected areas as the sum of the gray values of all the pixels in the selection divided by the number of pixels.

Mitochondrial Respiratory Chain Enzyme Activities by Spectrophotometer Analysis

Mitochondrial RC enzymes analysis was performed in cerebrum tissue as previously described (DiMauro, et al. 1987).

Statistical Methods

Data are expressed as the mean±SD of at least 3 experiments per group. Gehan-Breslow-Wilcoxon test was used to compare the survival proportion of each group of mice. A p-value of <0.05 was considered to be statistically significant.

Example 2—The Administration of dC/dT to Tk2$^{-/-}$ Mice Delayed the Clinical Onset of TK2 Deficiency and Increased Survival A dose of 260 and 520 mg/kg/day each of deoxynucleosides (dC/dT) were administered to the Tk2$^{-/-}$ mice. These doses of deoxynucleosides were the molar equivalent of 400 and 800 mg/kg/day of dCMP+dTMP respectively.

Figure 2:
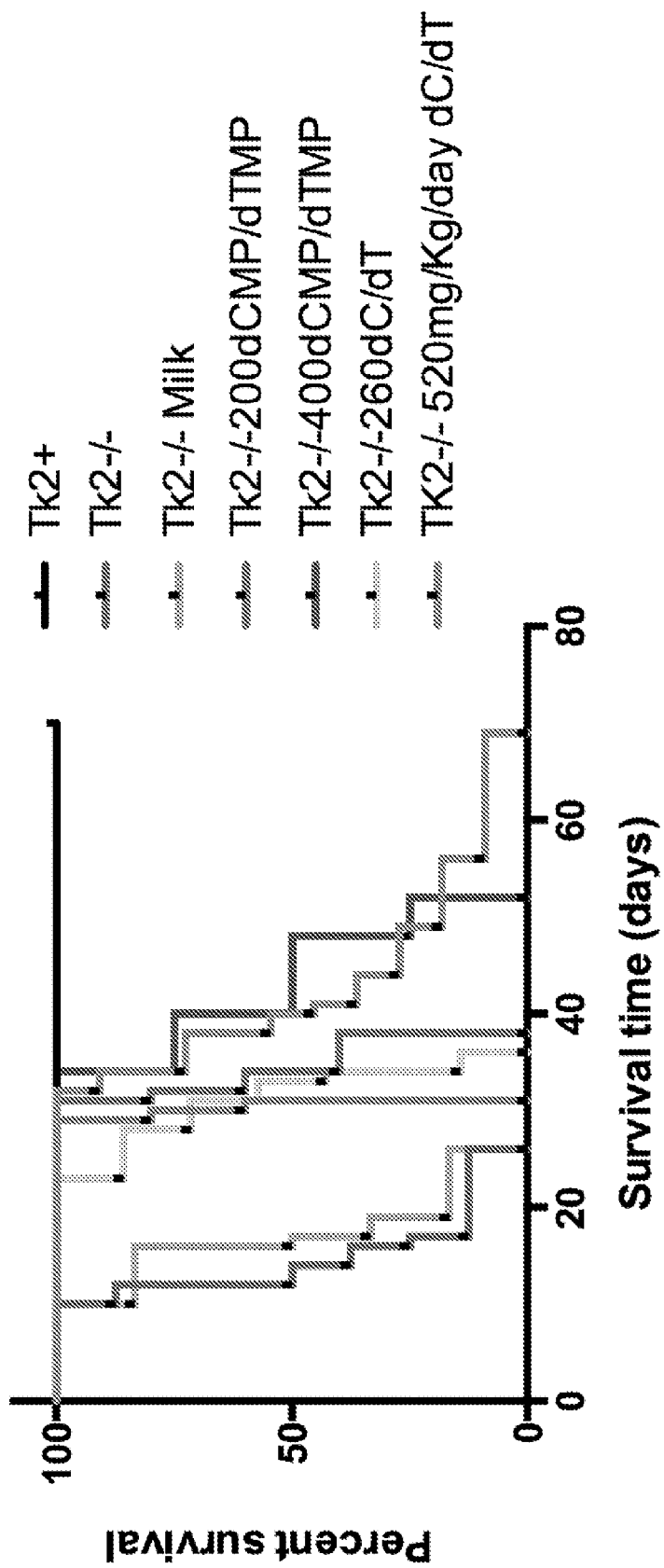
FIG. 2 depicts the survival curve of wild type ($Tk2^{+/+}$), and $Tk2^{-/-}$ mice with the following treatments: $Tk2^{-/-milk}$ vs $Tk2^{-/-200\ mg/kg/day\ dCMP+dTMP}$ p=0.0013; $Tk2^{-/-milk}$ vs $Tk2^{-/-260\ mg/kg/day\ dC+dT}$, p=00006; $Tk2^{-/-milk}$ vs $Tk2^{-/-520\ mg/kg/day\ dC+dT}$, p<0.0001; $Tk2^{-/-260\ mg/kg/day\ dC=dT}$ vs $Tk2^{-/-520\ mg/kg/day\ dCdT}$, p=0.0009, at postnatal day 4. N of each group indicated in figure, p-values determined by Mantel-Cox tests.

Mice treated with oral dC+dT (260 or 520 mg/kg/day from age 4 days) appeared normal until postnatal day 21 (FIG. 1). After age 21 days, mutant mice treated with 260 mg/kg/day dose (Tk2$^{-/-260\ mg/kg/day\ dC/dT}$) stopped gaining weight and developed mild head tremor and weakness that led to death at postnatal day 31±4.3 (FIG. 2).

Mutant mice treated with the 520 mg/kg/day dC+dT (Tk2$^{-/-520\ mg/Kg/day\ dC/dT}$) continued to gain weight for one additional week, but subsequently manifested deterioration similar to Tk2$^{-/-260mg/Kg/day\ dC/dT}$ and died at postnatal day 43±10. These results are comparable to those showed by Tk2$^{-/-}$ mice treated with 200 or 400 mg/kg/day of oral dCMP/dTMP treatment. Tk2$^{+260\ mg/kg/day\ dC/dT}$ and Tk2$^{+520\ mg/kg/day\ dC/dT}$ were followed until postnatal day 60. No side effects were observed.

As shown, the lifespan of the treated Tk2$^{-/-}$ was significantly increased. Untreated Tk2$^{-/-}$ mice showed a mean lifespan of 13 days, while treated mice survived a mean of 31 and 40 days with the 260 and 520 mg/kg/day dose, respectively (FIG. 2). Interestingly, one of the mice survived to postnatal day 56, which has been the longest lifespan for the Tk2 knock-in mouse model to date.

Example 3—Oral dC/dT Ameliorates Molecular Abnormalities in Brain and Liver

Figure 3:
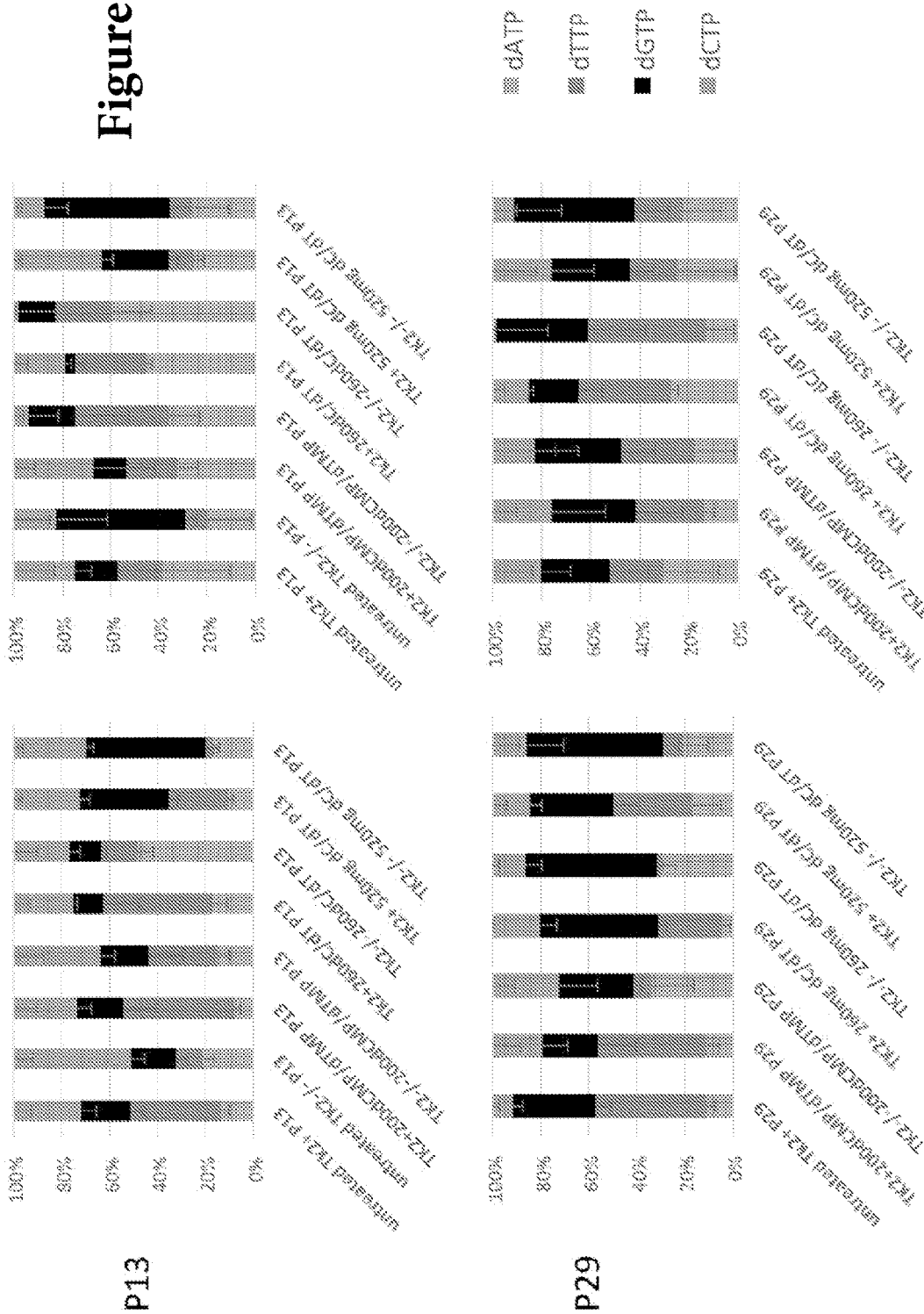
FIG. 3 are graphs of the relative proportions of dNTPs in isolated mitochondria from brain and liver tissue of wild type ($Tk2^{+/+}$), and $Tk2^{-/-}$, untreated or treated with 200 mg/kg/day dCMP and dAMP, or 260 mg/kg/day or 520 mg/kg/day of deoxycytidine (dC) and deoxythymidine (dT) at ages postnatal day 13 (top panels) and postnatal day 29 (bottom panels).

Measurement of dNTPs in mitochondrial extract showed that both Tk2$^{-/-260\ mg/Kg/day\ dC/dT}$ and Tk2$^{-/-520\ mg/Kg/day\ dC/dT}$ did not fully correct mitochondrial dNTP pool imbalances at postnatal day 13 and manifested variable effects in tissues with a completed rescue of dCTP deficits in brain, while dTTP was corrected in the liver. In contrast, deficiencies of dTTP in brain and dCTP in liver remained severe despite deoxynucleoside supplementation (FIG. 3).

Figure 4:
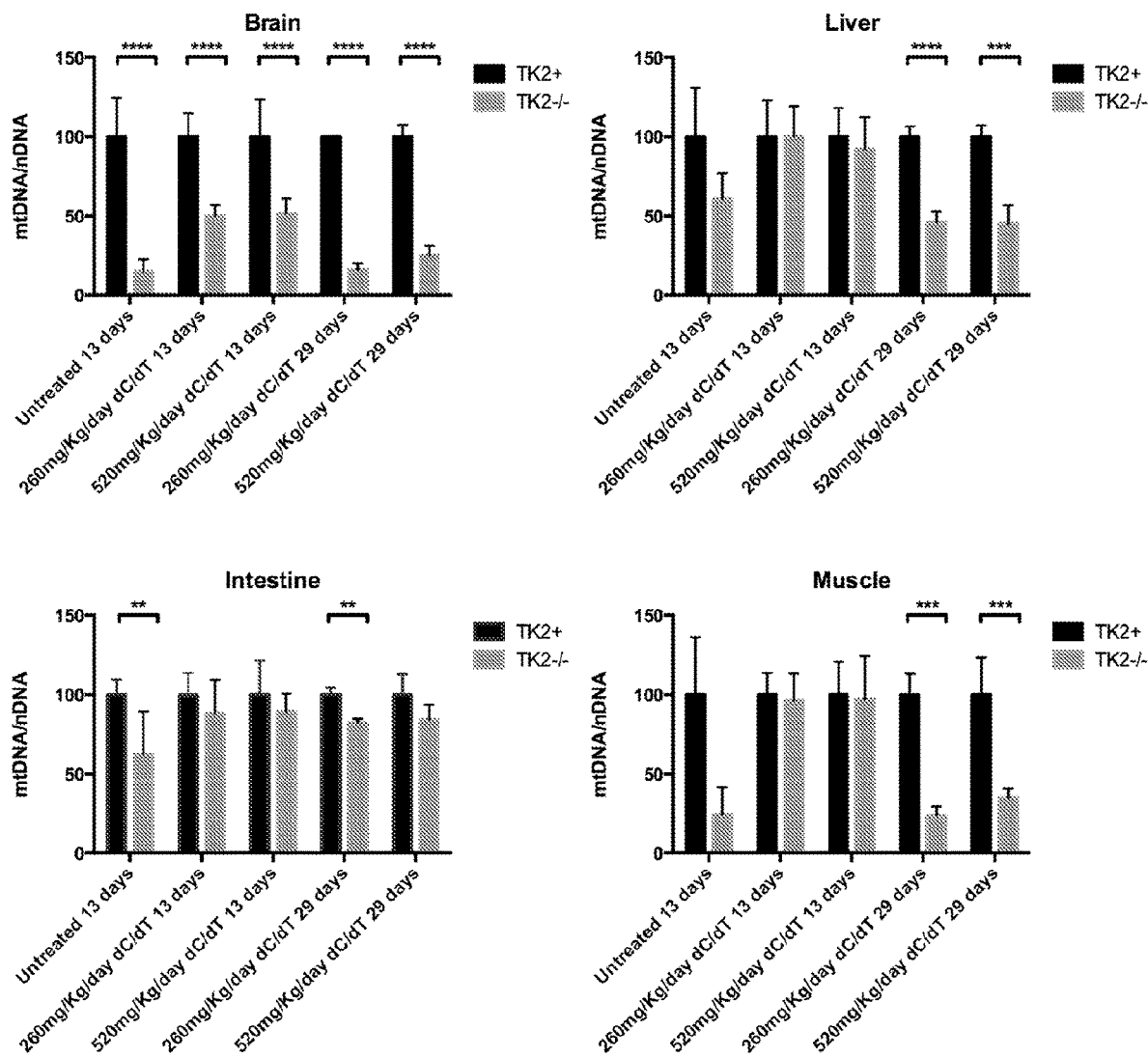
FIG. 4 are graphs showing the ratio of mtDNA/nDNA in brain, liver, intestine, and muscle in wild type Tk2 mice ($Tk2^{+/+}$) (left hand bar) as compared to $Tk2^{-/-}$ mice, untreated or treated with 260 mg/kg/day or 520 mg/kg/day of deoxycytidine (dC) and deoxythymidine (dT), at ages postnatal days 13 and 29. Data are represented as mean±standard deviation (SD) of the percent of mtDNA copies relative to $Tk2^+$. p-values were assessed by Mann-Whitney tests. (*p<0.05, p<0.01, *p<0.001, ****p<0.0001).
Figure 5:
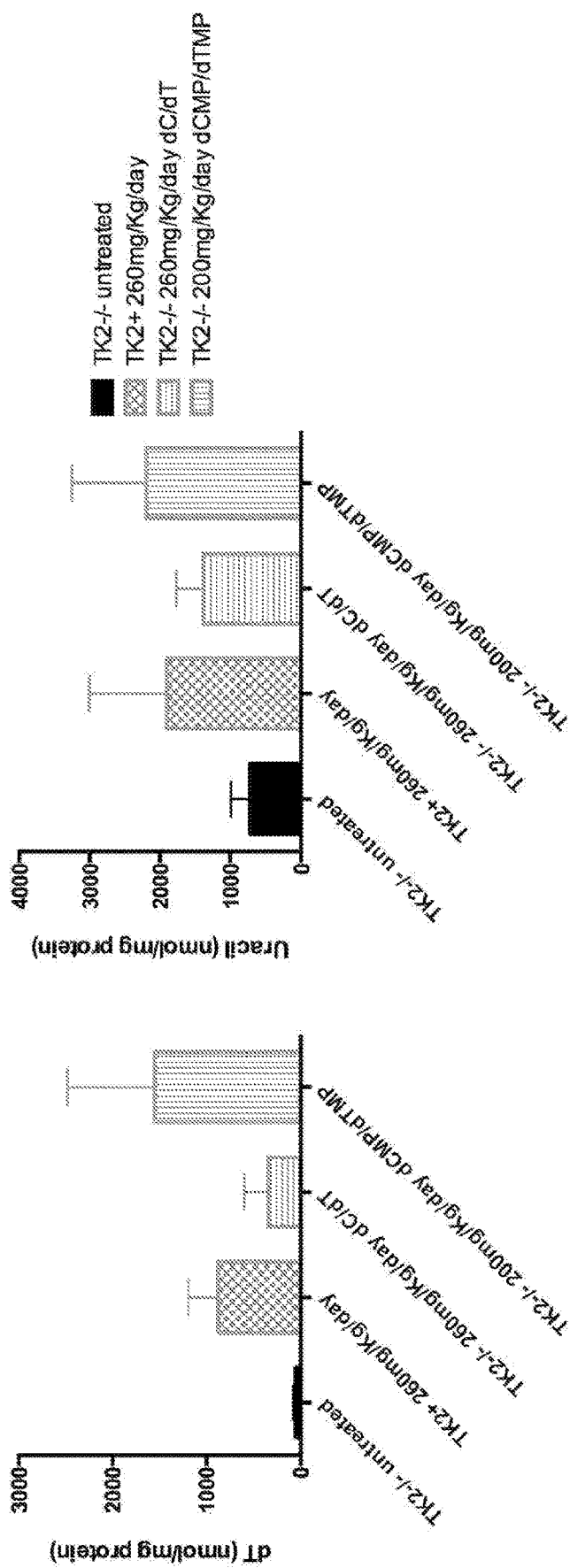
FIG. 5 are graphs depicting the results of HPLC measuring dT and uracil in plasma of untreated wild type ($Tk2^{+/+}$) mice, wild type ($Tk2^{+/+}$) mice treated with 260 mg/kg/day of deoxycytidine (dC) and deoxythymidine (dT), $Tk2^{-/-}$ mice treated with 260 mg/kg/day of deoxycytidine (dC) and deoxythymidine (dT), and $Tk2^{-/-}$ mice treated with 200 mg/kg/day of dCMP and dTMP, 30 minutes after treatment. Data are expressed as mean±SD.

In Tk2/$^{-/-260\ mg/Kg/day\ dC/dT}$ and Tk2$^{-/-520\ mg/Kg/day\ dC/dT}$ mice at postnatal day 13, the treatment prevented mtDNA depletion in heart, liver, kidney, intestine and muscle (FIG. 4). In contrast, mtDNA copy number was only partially ameliorated in brain at postnatal day 13 in a dose-dependent manner with mtDNA/nDNA ratios relative to control brain reaching 39% with 260 mg/kg/day of dC+dT and 52% with 520 mg/kg/day. Measurements of the bases dT and uracil in brain by HPLC showed higher levels in animals treated with dC+dT or with dCMP+dTMP (FIG. 5), further indicating that both deoxynucleosides and deoxynucleoside monophosphates cross the blood brain barrier. At postnatal day 29, mtDNA depletion was partially rescued by 260 and 520 mg/kg/day of dC+dT therapy in heart (40 and 35%), liver (46 and 45%), kidney (38 and 42%) and muscle (24 and 35%), but strikingly was fully rescued in intestine (82 and 84%) (FIG. 4).

Example 4—Oral dC/dT Ameliorates Biochemical Abnormalities in Brain

Figure 6:
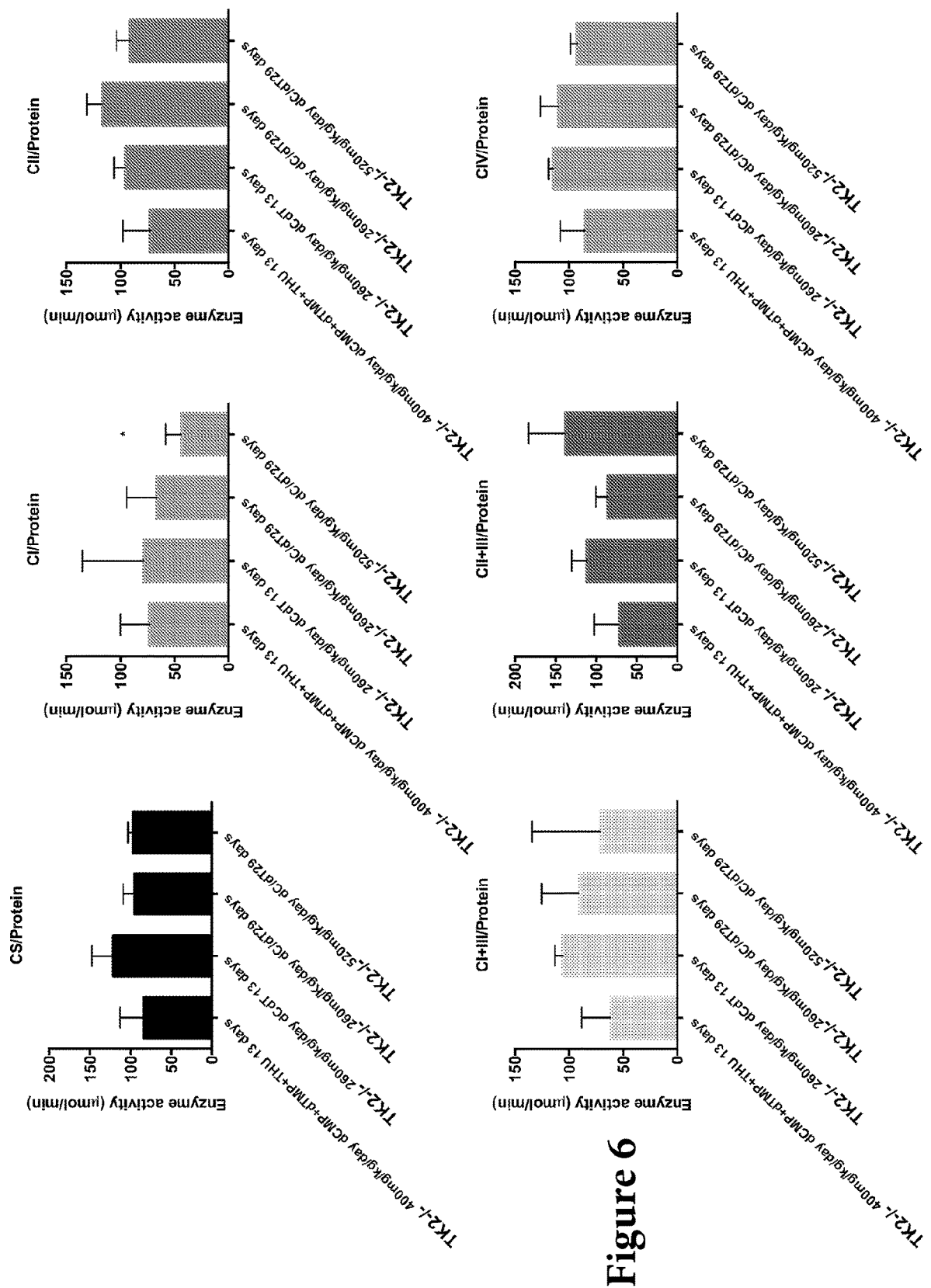
FIG. 6 are graphs of levels of respiratory chain enzyme activities in $Tk2^{-/-}$ mice treated with 400 mg/kg/day of dCMP and dTMP and THU at 13 days postnatal, 260 mg/kg/day of deoxycytidine (dC) and deoxythymidine (dT) at 13 and 29 days postnatal, or 520 mg/kg/day of deoxycytidine (dC) and deoxythymidine (dT) 29 days postnatal. Data are represented as the percent of the RCE activities in Tk2$^{-/-}$ mouse tissues normalized to protein levels and relative to Tk2$^+$ for each treatment. p-values determined by Mann-Whitney tests. *p<0.05.

Respiratory chain enzyme (RCE) activities and protein levels were completely rescued in brain of TK2$^{-/-260\ mg/Kg/day\ dC/dT}$ at postnatal day 13 (FIG. 6). RCE activities were also restored at postnatal day 29, and only a slight decrease of complex I activity could be observed in TK2$^{-/-52\ 0mg/Kg/day\ dC/dT}$ (FIG. 6). RCE protein levels in brain were partially restored at postnatal day 29 with higher levels in TK2$^{-/-520\ mg/Kg/day\ dc/dT}$ than in TK2$^{-/-260\ mg/Kg/day\ dC/dT}$ (FIG. 7). These differences in protein levels were consistent with the differences in mtDNA depletion in brains of treated mutant mice at postnatal day 29, and likely accounted for the prolonged survival observed with the higher dose.

Example 5—Administration of dC/dT in Patients with TK2 Deficiency Was Efficacious Symptoms, dosages, and outcomes of patients with TK2 deficiency who have received deoxynucleoside therapy under the supervision and control of the inventors are summarized below.

Patient 1

This patient was born in the United States in February 2011. His symptoms manifested at 12 months with hypotonic and a floppy head. He has never walked. He also has respiratory muscle weakness and was put on mechanical ventilation at 19 months, of which he is still on 24 hours/day. He has also been on a feeding tube since 19 months.

He was previously on 100 mg/kg/day and then 200 mg/kg/day of dCMP and dTMP. On this therapy, he was able to grip small objects and his weight increased from 10.4 kg to 19.5 kg.

In October of 2015, he began on 260 mg/kg/day of dC and dT which was increased to 340 mg/kg/day of dC and dT. After two months, he was moving his hands and head better, able to stand 5 minutes with support of a person, starting to cough, and his heart rate was slower (down from 140-170 bpm during day, to 100-120 bpm during day).

On Mar. 23, 2016, the dose was increased to 400 mg/kg/day of dC and dT. After 6 weeks on this therapy, he showed further improvements: he was able to sit in a chair about 5 hours/day; stood in a "Stander" for 1.5 hours; about to grab and hold small stuffed animals; pressed computer buttons;

untied his diapers and aimed his penis to wet the person changing the diaper; and held his knees flexed for a few seconds.

The only adverse effect seen during the treatment was diarrhea.

Patient 2

This patient was born in Spain in 1987. He began showing symptoms at 3 years of age including proximal muscle weakness. He lost the ability to walk at age 13 and was ventilated 24 hours a day. He was previously taking dAMP and dCMP at 200 mg/kg/day and showed a weight increase and a decrease of 24 to 22 hours a day on ventilation.

He has been on deoxynucleoside therapy since June of 2015 at 400 mg/kg/day dC and dT, and has shown improvement in muscle strength, his weight and ventilation have stabilized, and he is enjoying a better quality of life.

The only adverse effects seen during the treatment was diarrhea and hair loss.

Patient 3

This patient was born in Spain in 1985. His symptoms began at 6 years old with facial, proximal, and axial muscle weakness. He started 200 mg/kg/day of dT and dC in June of 2015 and to date, his condition has improved with improvements in 6 minute walk test, time to get up and go, and climb up and down 4 steps.

The only adverse effect seen during the treatment was diarrhea.

Patient 4

This patient was born in Spain in February 2009. His symptoms manifested at six months with failure to thrive. He started on 230 mg/kg/day of dC and dT in July of 2015. By January of 2016, he showed improvement in his condition and was eating better.

There were no observed adverse effects.

Patient 5

This patient was born in Spain in 1957 and began to have symptoms at 50 years old of orthopnea, and diaphragmatic weakness. He is on BiPAP at night. He started on 200 mg/kg/day of dC and dT in November of 2015.

There were no observed adverse effects.

Patient 6 This patient was born in Spain in October 2011, and starting showing symptoms at 15 months, including hypotonia and weakness. He lost ambulation at 22 months, and has respiratory muscle weakness. He started mechanical ventilation at 16 months and is currently on BiPAP twelve hours a day. He was previously on dCMP and dAMP at 100 mg/kg/day that was increased to 400 mg/kg/day. His strength as shown by Egen Klassification scale improved (28/30 to 13/30) and his weight increased from 9.8 kg to 12.3 kg.

He began deoxynucleoside therapy in April 2015 at 400 mg/kg/day of dC and dT. In October of 2015, his change in Egen Klassification scale went from 13/30 to 11/30 and his weight increased to 16.5 kg from 12.3 kg.

There were no observed adverse effects.

Patient 7

This patient was born in Spain in November of 2012. He started showing symptoms at 17 months including weakness and hypotonia. He lost ambulation at 22 months and started mechanical ventilation at 29 months. He was previously on dCMP and dAMP at 100 mg/kg/day that was increased to 400 mg/kg/day. His strength as shown by Egen Klassification scale improved (30/30 to 24/30) and his weight increased from 11 kg to 15.7 kg.

He started deoxynucleoside therapy in April 2015 with a dose of 400 mg/kg/day dT and dC. In November of 2015, his change in Egen Klassification scale went from 24/30 to 19/30 and his weight increased to 17 kg from 15.7 kg.

There were no observed adverse effects.

Patient 8

This patient was born in Chile in September of 1989 and started showing symptoms at 11 months with frequent falls and progressive gait impairment. She lost the ability to walk alone at about 4 years of age. She had been on nucleotide therapy previously and showed improvement in her mobility, including walking unassisted, standing longer, climbing stairs, attending gym class, and attending to personal needs.

She switched to deoxynucleoside therapy in February of 2016 at a dose of 260 mg/kg/day of dC and dT, and then increased to a dose of 400 mg/kg/day of dC and dT in May of 2016 and continued to show improvement.

There were no observed adverse effects.

Patient 9

This patient was born in Guatemala in September of 1989. He began 130 mg/kg/day of dC and dT in August of 2015 and increased to 260 mg/kg/day in February of 2016. He has shown improved energy.

There were no observed adverse effects.

REFERENCES

Akman, et al. (2008) Thymidine kinase 2 (H126N) knock in mice show the essential role of balanced deoxynucleotide pools for mitochondrial DNA maintenance. *Hum. Mol Genet.* 17:2433-2440

Alston, et al. (2013) Late-onset respiratory failure due to TK2 mutations causing multiple mtDNA deletions. *Neurology* 81:2051-3

Bartesaghi, et al. (2010) Loss of thymidine kinase 2 alters neuronal bioenergetics and leads to neurodegeneration. *Hum. Mol. Genet.* 19:1669-77

Béhin, et al. (2012) Adult cases of mitochondrial DNA depletion due to TK2 defect An expanding spectrum. *Neurology* 78:644-648

Blakely, et al. (2008) Novel mutations in the TK2 gene associated with fatal mitochondrial DNA depletion myopathy. *Neuromuscular Disorders* 18:557-560

Bourdon, et al. (2007) Mutation of RRM2B, encoding p53-controlled ribonucleotide reductase (p53R2), causes severe mitochondrial DNA depletion. *Nature Genetics* 39:776-780

Carrozzo, et al. (2003) Mutation analysis in 16 patients with mtDNA depletion. *Hum. Mutat.* 21:453-454

Chanprasert, et al. (2013) Molecular and clinical characterization of the myopathic form of mitochondrial DNA depletion syndrome caused by mutations in the thymidine kinase (TK2) gene. *Mol. Genet. Metab.* 110:153-61

Chanprasert, et al. (2012) TK2-Related Mitochondrial DNA Depletion Syndrome, Myopathic Form. *GeneReviews® Internet*, Dec. 6, 2012

Collins, et al. (2009) Progressive myofiber loss with extensive fibro-fatty replacement in a child with mitochondrial DNA depletion syndrome and novel thymidine kinase 2 gene mutations. *Neuromuscular Disorders* 19:784-787

Copeland (2008) Inherited mitochondrial diseases of DNA replication. *Ann. Rev. Med.* 59:131-146

DiMauro, et al. (1987) Cytochrome c oxidase deficiency in Leigh syndrome. *Ann. Neurol.* 22:498-506

DiMauro, Schon. (2003) Mitochondrial respiratory-chain diseases. *New England Journal of Medicine* 348:2656-2668

DiMauro, Hirano. (2005) Mitochondrial encephalomyopathies: an update. *Neuromuscul. Disord.* 15:276-286

Dorado, et al. (2011) Onset and organ specificity of Tk2 deficiency depends on Tk1 down-regulation and transcriptional compensation. *Hum. Mol. Genet.* 20:155-64

Elpeleg, et al. (2005) Deficiency of the ADP-forming succinyl-CoA synthase activity is associated with encephalomyopathy and mitochondrial DNA depletion. *Am. J. Hum. Genet.* 76:1081-1086

Ferraro, et al. (2010) Quantitation of cellular deoxynucleoside triphosphates. *Nucleic Acids Research* 38:e85

Calbiati, el al (2006) New mutations in TK2 gene associated with mitochondrial DNA depletion. *Pediatr. Neurol.* 34:177-185

Garone, et al. (2012). MIPV17 Mutations Causing Adult-Onset Multisystemic Disorder With Multiple Mitochondrial DNA Deletions. *Arch Neurol* 69:1648-1651

Garone, et al. (2014). Deoxypyrimidine monophosphate bypass therapy for thymidine kinase 2 deficiency. *EMBO Mol Mcd* 6:1016-1027

Garone, et al. (2016) in preparation, "Phenotypic Spectrum and Retrospective Natural History of Thymidine Kinase 2 Deficiency"

Gotz, et al. (2008) Thymidine kinase 2 defects can cause multi-tissue mtDNA depletion syndrome. *Brain* 131: 2841-2850

Hirano, et al. (2001) Defects of intergenomic communication: autosomal disorders that cause multiple deletions and depletion of mitochondrial DNA. *Semin. Cell. Develop. Biol.* 12:417-427

Hirano, et al. (2004) MtDNA maintenance and stability genes: MNGIE and mtDNA depletion syndromes. In: Kohler, Bauer, editors. *Mitochondrial Function and Biogenetics*. Berlin: Springer-Verlag. p. 177-200

Leshinsky-Silver, et al.(2008) A defect in the thymidine kinase 2 gene causing isolated mitochondrial myopathy without mtDNA depletion. *Eur. J. Paediatr. Neurol.* 12:309-13

Lesko, et al. (2010) Two novel mutations in thymidine kinase-2 cause early onset fatal encephalomyopathy and severe mtDNA depletion. *Neuromuscul. Disord.* 20:198-203

Longley, et al. (2006). Mutant POLG2 disrupts DNA polymerase gamma subunits and causes progressive external ophthalmoplegia. *Am J Hum Genet.* 78:1026-1034

Lopez, et al. (2009) Unbalanced deoxynucleotide pools cause mitochondrial DNA instability in thymidine phosphorylase deficient mice. *Human Molecular Genetics* 18:714-22

Mancuso, et al. (2003) Mitochondrial myopathy of childhood associated with mitochondrial DNA depletion and a homozygous mutation (T77M) in the TK2 gene. *Arch. Neurol.* 60:1007-9

Mancuso, et al. (2002) Mitochondrial DNA depletion: mutations in thymidine kinase gene with myopathy and SMA. *Neurology.* 59:1197-202

Mandel, et al. (2001) The deoxyguanosine kinase gene is mutated in individuals with depleted hepatocerebral mitochondrial DNA. *Nature Genet.* 29:337-341

Martí, et al. (2010) Hearing loss in a patient with the myopathic form of mitochondrial DNA depletion syndrome and a novel mutation in the TK2 gene. *Pediatr. Res.* 68:151-4

Martí, et al. (2012a) Measurement of mitochondrial dNTP pools. *Methods Mol. Biol.* 837:135-148

Martí, et al. (2012b) Assessment of thymidine phosphorylase function: measurement of plasma thymidine (and deoxyuridine) and thymidine phosphorylase activity. *Methods Mol. Biol.* 837: 121-133

Naviaux, Nguyen. (2004) POLG mutations associated with Alpers' syndrome and mitochondrial DNA depletion. *Ann. Neurol.* 55:706-712

Nishino, et al. (1999). Thymidine phosphorylase gene mutations in MNGIE, a human mitochondrial disorder. *Science* 283:689-692.

Oskoui, et al. (2006) Clinical spectrum of mitochondrial DNA depletion due to mutations in the thymidine kinase 2gene. *Arch. Neurol.* 63:1122-1126.

Ostergaard, et al. (2007) Deficiency of the alpha subunit of succinate-coenzyme A ligase causes fatal infantile lactic acidosis with mitochondrial DNA depletion. *Am. J. Hum. Genet.* 81: 383-387

Paradas, et al. (2012) TK2 mutation presenting as indolent myopathy. Neurology 29:504-506

Ronchi, et al. (2012). Next-generation sequencing reveals DGUOK mutations in adult patients with mitochondrial DNA multiple deletions. *Brain* 135:3404-3415.

Roos, et al. (2014) Mitochondrial DNA depletion in single fibers in a patient with novel TK2 mutations. *Neuromuscul. Disord.* 24:713-20

Saada, et al. (2001) Mutant mitochondrial thymidine kinase in mitochondrial DNA depletion myopathy. *Nature Genet.* 29:342-344

Saada, et al. (2003) Mitochondrial deoxyribonucleoside triphosphate pools in thymidine kinase 2 deficiency. *Biochem. Biophys. Res. Commun.* 310:963-966

Sarzi, et al. (2007) Twinkle helicase (PEO1) gene mutation causes mitochondrial DNA depletion. *Ann. Neurol.* 62: 579-587

Spelbrink, et al. (2001). Human mitochondrial DNA deletions associated with mutations in the gene encoding Twinkle, a phage T7 gene 4-like protein localized in mitochondria. *Nature Genet.* 28:223-231

Spinazzola, et al. (2006) MPV17 encodes an inner mitochondrial membrane protein and is mutated in infantile hepatic mitochondrial DNA depletion. *Nature Genet.* 38:570-575

Tulinius, et al. (2005) Novel mutations in the thymidine kinase 2 gene (TK2) associated with fatal mitochondrial myopathy and mitochondrial DNA depletion. *Neuromuscul. Disord.* 15:412-415

Tyynismaa, et al. (2012) Thymidine kinase 2 mutations in autosomal recessive progressive external ophthalmoplegia with multiple mitochondrial DNA deletions. *Hum. Mol. Genet.* 21:66-75

Tyynismaa, et al. (2009). A heterozygous truncating mutation in RRM2B causes autosomal-dominant progressive external ophthalmoplegia with multiple mtDNA deletions. *Am. J. Hum. Genet.* 85: 290-295

Van Goethem, et al. (2001) Mutation of POLG is associated with progressive external ophthalmoplegia characterized by mtDNA deletions. *Nature Genet.* 28:211-212.

Vilà, et al. (2003) Reversion of mtDNA depletion in a patient with TK2 deficiency. *Neurology* 60:1203-1205

Wang, et al. (2005) Molecular insight into mitochondrial DNA depletion syndrome in two patients with novel mutations in the deoxyguanosine kinase and thymidine kinase 2 genes. *Mol. Genet. Metab.* 84:75-82.

The invention claimed is:

1. A method of treating mitochondrial DNA depletion syndrome in a human subject in need thereof comprising administering to the subject a therapeutically effective amount of a composition comprising at least one deoxynucleoside, wherein the mitochondrial DNA depletion syndrome is characterized by at least one mutation in a gene which is DGUOK and wherein the therapeutically effective amount is between about 200 mg/kg/day and 600 mg/kg/day of the at least one deoxynucleoside in the composition and the composition is administered to the subject parenterally.

2. The method of claim 1, wherein the composition is administered intravenously.

3. The method of claim 1, wherein the composition is administered one time a day, two times a day, three times daily, four times daily, five times daily or six times daily.

4. A method of treating mitochondrial DNA depletion syndrome in a human subject in need thereof comprising administering to the subject a therapeutically effective amount of a composition comprising at least one deoxynucleoside, wherein the mitochondrial DNA depletion syndrome is characterized by at least one mutation in a gene chosen from the group consisting of: TYMP and RRM2B and wherein the therapeutically effective amount is between about 200 mg/kg/day and 600 mg/kg/day of the at least one deoxynucleoside in the composition and the composition is administered to the subject parenterally.

5. The method of claim 4, wherein the composition is administered intravenously.

6. The method of claim 4, wherein the composition is administered one time a day, two times a day, three times daily, four times daily, five times daily or six times daily.

7. A method of treating mitochondrial DNA depletion syndrome in a human subject in need thereof comprising administering to the subject a therapeutically effective amount of a composition comprising at least one deoxynucleoside, wherein the mitochondrial DNA depletion syndrome is characterized by at least one mutation in a gene chosen from the group consisting of: TK2, DGUOK; TYMP; and RRM2B and wherein the therapeutically effective amount is between about 200 mg/kg/day and 600 mg/kg/day of the at least one deoxynucleoside in the composition and the composition is administered to the subject intrathecally.

8. The method of claim 1, wherein the composition comprises dG and/or dA.

9. The method of claim 4, wherein the composition comprises dA, dG, dC, or dT, or mixtures thereof.

* * * * *